United States Patent [19]

Moedritzer

[11] 4,087,403
[45] May 2, 1978

[54] POLYPHOSPHINATE FLAME RETARDANTS

[75] Inventor: Kurt Moedritzer, Webster Groves, Mo.

[73] Assignee: Monsanto Company, St. Louis, Mo.

[21] Appl. No.: 662,766

[22] Filed: Mar. 1, 1976

[51] Int. Cl.² .............................................. C08K 5/53
[52] U.S. Cl. ............................. 260/45.7 P; 260/2 P; 260/47 P; 260/857 R; 260/860; 260/931; 260/973
[58] Field of Search ..................... 260/2.5 AJ, 45.7 P, 260/75 P, 931, 973, 47 P, 2 P, 857 R, 860

[56] References Cited

U.S. PATENT DOCUMENTS

| | | | |
|---|---|---|---|
| 3,027,349 | 3/1962 | Bahr et al. | 260/931 |
| 3,161,607 | 12/1964 | Garner | 260/2 P |
| 3,314,900 | 4/1967 | Uhing | 260/2 P |
| 3,371,131 | 2/1968 | Carson et al. | 260/931 |
| 3,855,352 | 12/1974 | Moedritzer | 260/873 |
| 3,875,263 | 4/1975 | Herwig et al. | 260/928 |
| 3,927,231 | 12/1975 | Desitter et al. | 260/860 |
| 3,928,283 | 12/1975 | Masai et al. | 260/45.7 P |
| 3,959,213 | 5/1976 | Gilkey et al. | 260/45.7 P |
| 3,993,623 | 11/1976 | Moedritzer et al. | 260/45.95 D |

*Primary Examiner*—Melvyn I. Marquis
*Assistant Examiner*—R. A. White
*Attorney, Agent, or Firm*—Herman O. Bauermeister

[57] ABSTRACT

The invention relates to novel phosphinate polymers having the formula

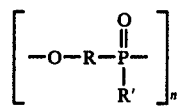

wherein R is a phenylene or naphthylene group in which the O substituent is nonvicinal to the

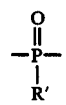

group, R' is an alkyl group of 1 to 15 carbon atoms or an aryl group of 6 to 15 carbon atoms, and $n$ is from 5 to 50 units. The invention also relates to a process for the production of the novel polymeric phosphinate resins, and to combinations of such polymeric phosphinates with organic polymers such as polyesters, e.g., polyethylene terepthalate, and polyamides, e.g., hexamethylene adipamide. The combination of the present polymeric phosphinates with the organic polymers makes it possible to obtain flame retardant products, for example fibers suitable for carpeting and clothing.

11 Claims, No Drawings

POLYPHOSPHINATE FLAME RETARDANTS

FIELD OF THE INVENTION

The present invention relates to novel polymeric phosphinate resins and combinations of such polymeric phosphinates with organic polymers such as polyesters, e.g., polyethylene terephthalate, and polyamides, e.g., hexamethylene adipamide. The physical or chemical combination of the present polymeric phosphinates with the organic polymers makes it possible to obtain flame retardant products, for example fibers suitable for carpeting and clothing. Specifically the invention relates to novel phosphinate polymers having the formula

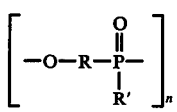

wherein R is a phenylene or naphthylene group in which the O substituent is non-vicinal to the

group, R' is an alkyl group of 1 to 15 carbon atoms, or an aryl group of 6 to 15 carbon atoms and n is from 5 to 50 units.

BACKGROUND OF THE INVENTION

Many flame retarding agents and methods of application have been developed in attempts to obtain flame resistant textile materials and thermoplastic or thermosetting resin compositions.

The production of organic resin compositions which are flame retardant is of considerable commercial importance. For example, such articles as fibers, films, castings, moldings, foamed or laminated structures and the like are required, or are at least desired, to be resistant to fire and flame and to possess the ability to endure heat without deterioration. The use of various materials incorporated into thermoplastic resins so as to improve the flame retardancy thereof has been known. Many compounds have been commercially available for such use, among them being chlorostyrene copolymers, chlorinated paraffin wax in admixture with triphenyl phosphate, chlorinated paraffins and antimony compounds, as well as antimony oxide-chlorinated hydrocarbon mixtures. A problem associated with these compounds has been however, the fact that generally a large amount, i.e., upwards of 35 percent of additive, must be incorporated into the resin in order to make it sufficiently flame retardant. Such large amounts of additive may deleteriously affect the physicl characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

Phosphorus compounds have been employed in various flame retardant products. However when some of the compounds of the prior art are employed with dissolved or molten organic polymers such as polyesters and polyamides, for example in fiber production, difficulties are encountered.

Some types of organic polyphosphonate compounds when used in extrusion processes, such as in the fiber spinning of polyesters, e.g., polyethylene terephthalate or polyamides, e.g., 6,6-nylon have been found to cause crosslinking. This results in severe problems of nodule formation during the spinning operation, with the result that spinnerettes are clogged and fibers cannot be handled in drawing, heat treating, washing and dyeing operations. This is because the nodules cause irregularities and thick sections in the fibers, so that the spinning operations become impossible.

In contrast to such prior art, the present invention utilizes polymeric phosphinate resins having a P-O-C(aromatic) linkage in the backbone of the polymer. These polymers have been found to be a useful combination together with polyester or polyamide products, so that the modified organic polyester or polyamide can be melted and spun from an orifice to yield smooth fibers which are readily stretched and washed for utilization in weaving operations. The present modified organic polymers are also characterized by improved flame retardancy properties.

The polymeric resins of the present inention have the general molecular structure as condensed products

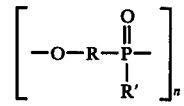

wherein R is a phenylene or naphthylene group in which the O substituent is non-vicinal to the

group, R' is an alkyl group of 1 to 15 carbon atoms or an aryl group of 6 to 15 carbon atoms, and n is from 5 to 50 units. The successive repeating units provide a P-O-C aromatic linkage which is desirable for fire-retardant properties, and thermal stability. The provision of oxygen atoms in the backbone of the polymeric molecular structure as P-O-C(aromatic), also imparts resistance to hydrolysis, since the oxygen is less accessible to hydrolyzing agents such as acids, bases, water and atmospheric humidity.

The use of an O-substitute which is non-vicinal refers to the employment of meta and para positions on the R ring as a phenyl relative to the position of the phosphorus. With naphthyl as R, the O-substituent is also non vicinal, e.g., the 1.3, 1.4, 1.5, 2.4, and 1.6 positions, for the two substituents. The substituent groups are thus located on carbon atoms separated by at least one carbon atom. The R and R' groups may also have chlorine or bromine substituents.

The general process for preparing the present polyphosphinate resins comprises dehydrohalogenating at a temperature of 50° C to 300° C a monomeric compound having the general formula

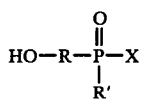

where X is chlorine or bromine, and R and R' are as described above.

The invention also includes the combination of an organic polymer such as a polyester or a polyamide together with the above polyphosphinate resins. The resin may be used as an additive applied to the organic polymer in a molten state before spinning. However, the polyphosphinate resin may also be applied from a solution (e.g., in an aliphatic alcohol such as methanol, ethanol or iso-propanol, or a ketone such as methylethyl ketone) directly to sheets or other shaped forms, including fibers or fabrics of the organic polymer.

The invention also includes copolymers of the above organic polymers together with the present polyphosphinates, made, e.g. as by ester interchange. Block copolymers can also be formed as a result of ester interchange using standard techniques.

The polymeric phosphinates of the present invention can be prepared beginning with a phenolic substituted phosphinic acid compound having the general formula, utilizing the R and R' symbols as above,

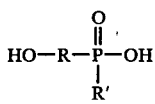

This is treated with a halogenating agent, such as thionyl chloride or thionyl bromide, to give a halide derivative having the following general formula, where X is chlorine or bromine.

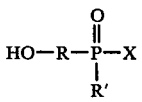

A specific halogenation for example is carried out by employing thionyl chloride with p-HO-C$_6$H$_4$P(C$_6$H$_5$)OOH (p-hydroxyphenylphenylphosphinic acid). The halogenated product is p-HOC$_6$H$_4$P(C$_6$H$_5$)OCl (p-hydroxyphenylphenylphosphinic chloride.) The latter intermediate is subjected to a dehydrohalogenation, such as by heating at a temperature of from 50° C to 300° C. The equation for this reaction employing the above general compounds is as follows:

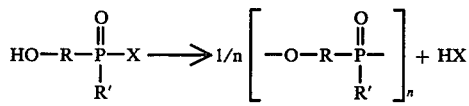

The dehydrohalogenation does not require a solvent, although a nonreactive solvent such as benzene, xylene, or petroleum ether may be employed. A catalyst is also unnecessary, although the reaction may be accelerated by the use of a catalyst such as pyridine hydrochloride or piperidine hydrochloride. The dehydrohalogenation can be conducted at elevated pressure, atmospheric conditions or a vacuum, with vacuum conditions being preferred in order to remove the hydrogen halide as evolved.

The end groups of the condensed products as usually H at the phenolic oxygen, and a halogen such as chlorine at the phosphorus. However, other chain terminating agents, such as an —OR, an OH or a O-P-(O-phenyl)$_2$ group at the phosphorus can be provided such as by treatment with alcohol, water, or an ester of phosphorus acid, e.g., triphenyl phosphite, respectively.

The compounds of the present invention are useful in fire-retardant materials. The method of testing fire-retardant properties is A.S.T.M. Designation D 2863-70, entitled "Standard Method of Test for Flammability of Plastics Using the Oxygen Index Method."

In the oxygen index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75mm minimum inside diameter and 450 mm minimum height. At the bottom of the tube is a bed of glass beads about 100mm deep to mix and distribute the gas mixture. Within the glass tube used as the test column there is a specimen holder to support the treated plastic material, while the apparartus is supplied with oxygen and nitrogen flow and control devices. The apparatus is also provided with an igniter which is a separate tube through which a combustible gas such as natural gas is used to ignite the test specimen. In the present testing program glass scrim supported molded sheets of nylon or polyethylene terephthalate ca. 0.2mm thick and about 25mm by 100 mm in size are used as the test specimens which are prepared from nylon or polyethylene terephthalate powder and 1% to 20% by weight of the fire retardant additive; the data in the present work correspond to about 10% by weight of additive. As a result of the molding of the organic polymer, e.g., nylon or polyethylene terephthalate, and the additive, an itimate admixture or melt of the molecules of the components is obtained.

In conducting the test, the specimen is clamped in the holder in the test column after which the desired initial concentration of oxygen is introduced to the ignited specimen. A number of tests are conducted to determine the minimum concentration of oxygen that will just support combustion.

The present condensation products are useful in combination with organic polymers generally to reduce combustibility. The normally flammable organic polymers which are rendered fire retardant in accordance with the invention may be natural or synthetic but are preferably a solid synthetic polymer, more preferably a nylon or ester type polymer. Examples of the polymer are cotton, wool, silk, paper, natural rubber, and paint, and also the high molecular weight homopolymers and copolymers of amides, e.g., (nylon 66 and nylon 6). Other polymers include esters such as polyethylene terephthalate, and polymers of other unsaturated aliphatic and aromatic hydrocarbons, e.g., ethylene, propylene, butylene, styrene, etc., and also acrylic polymers, e.g., polyacrylonitrile, polymethyl methacrylate, alkyd resins, as well as cellulose derivatives, e.g., cellulose acetate, methyl cellulose, etc. Still other polymers include epoxy reins, furan resins, isocyanate resins such as polyurethanes, melamine resins, vinyl resins such as polyvinyl acetate and polyvinyl chloride, resorcinol resins, synthetic rubbers such as polyisoprene, polybutadiene-acrylonitrile copolymers, butadiene-styrene polymers, butyl rubber, neoprene rubber, ABS resins and mixtures thereof. Since the compositions of the invention are unusually effective flame retardants they are normally combined in flame retarding proportions with the organic polymer at relatively low concentrations, e.g., about 1–20 wt. %, preferably about 3–15% based on the weight of the polymeric substrate, such as by milling, or impregnation, e.g., from a water or alcohol dispersion or solution, or by dissolving or dispering in the molten polymer before extrusion such as in the form of fibers or sheets. It should be noted that it is within the scope of the invention to incorporate such ingredients as dyes, pigments, stabilizers, antioxidants, antistatic agents and the like into the novel compositions.

The following examples illustrate specific embodiments of the invention but are not restrictive of the scope of the invention:

EXAMPLE 1

This example shows the preparation of the starting monomer.

A charge of p-bromoanisol is employed in the proportion of 84.7g (0.45 mole). The above charge is placed together with 9.0 grams of nickel bromide as a catalyst in a 250 ml round bottom flask fitted with an ice cooled condensation head, a dropping funnel, and a thermometer. The other reactant is diethyl phenylphosphonite $C_6H_5P(OC_2H_5)_2$ employed in the proportion of 86.58 grams (0.44 moles).

The latter compound is added dropwise to the reaction mixture which is maintained at 175° C. The mixture slowly darkens during this addition which is conducted over a period of about 2 hours. The reaction vessel is then allowed to cool and the reaction mixture purified. A total of 48 grams of ethyl bromide is collected, indicating the formation of about a 100% yield of ethyl p-methoxyphenylphenylphosphinate. The latter is hydrolyzed (by refluxing with concentrated HCl) to p-methoxyphenylphenylphosphinic acid and then demethylated by treatment with boron tribromide to give the desired p-hydroxyphenylphenylphosphinic acid, the starting material of Example 2.

EXAMPLE 2

The reactor vessel is charged with 2.5 grams of purified thionylchloride (21.0 mmole), together with 5 ml of dry benzene and 4.684 gram (20 mmole) of p-$HOC_6H_4P(C_6H_5)OOH$ (p-hydroxyphenylphenylphosphinic acid). The vessel is sealed and shaken at room temperature for 8 hours. The vessel is then charged with 5 additional grams of thionylchloride and further shaking continued until the solids have all gone into solution. After 24 hours of agitation, the vessel is opened and the solution evaporated free of solvent at room temperature over a vacuum. The reaction mixture is a viscous liquid which upon heating to 150° C at atmospheric pressure becomes liquid. Heating the mixture results in evolution of hydrogen chloride. The dehydrochlorination proceeds without a catalyst, although the addition of 0.1 wt. % of pyridine hydrochloride accelerates the dehydrochlorination. The reaction mixture is heated to a temperature of 250° C for 2 hours.

The reaction mixture upon further heating under oil pump vacuum (about 0.1 mm Hg) and the use of a dry ice trap to collect volatile components results in the collection of unreacted materials in the cold trap, and the production of a residual product of the above formula in the reaction vessel. The product is soluble in methanol, methyl ethyl ketone and is precipitated from such solutions by the addition of water. The melting point of the product, condensed p-hydroxyphenylphenylphosphinate, is about 225° C, and the molecular weight is equivalent to about 10 monomeric units, e.g., a molecular weight of about 2050. The end groups are H on the oxygen and a chlorine at the phosphorus.

When the meta isomer is used as the starting compound, the meta-substituted polymer is obtained.

EXAMPLE 3

A para-substituted polymeric composition of Example 2 is used as an additive chemical in order to impart fire-retardant properties to polyethylene terephthalate. The amount of the additive is 10% by wt. of the total composition. The polyethylene terephthalate is milled with the additive and is then formed into sheets which are 0.07 inches thick for testing purposes. Utilizing the method described above for measurement of flame-retardancy, the oxygen index value is 24.0, in comparison to unmodified polyethylene terephthalate which has a value of 19.0. The meta-isomer of the polymer has similar properties.

EXAMPLE 4

When the procedures of Examples 1 and 2 begin with the R' substituent being methyl, the starting materials utilized in the same molar proportions are p-bromoanisol and diethylmethylphosphonite. The monomer thus obtained is ethyl p-methoxyphenylmethylphosphinate. The polymeric product is condensed p-hydroxyphenylmethylphosphinate, of about the same molecular weight, and fire retardant properties (with respect to polyethylene terephthalate and nylon 6,6) as in Example 2.

EXAMPLE 5

Modification of the procedure of Examples 1 and 2 utilizing a naphthyl substituent begins with the starting materials of 1,4-bromomethoxynaphthalene and diethylphenylphosphonite. In this way the monomeric product is 4-methoxynaphthylphenylphosphinate and the polymeric products condensed 4-hydroxynaphthylphenylphosphinate.

The molecular weight and fire retardant properties (with respect to polyethylene terephthalate and nylon 6,6) of the product are similar to those of Example 2.

EXAMPLE 6

The formulation of the polyphosphinates of the present invention with an organic resin can be carried out by adding the phosphinate product to the desired organic polymer. Thus a molten form of polyethylene terephthalate is utilized as the organic polymer, to which the polyphoshphinate is added. After mixing, the molten polymer is extruded to yield fibers or other desired shaped products. Another polyester which is improved in fire retardant properties by the incorporation thereof of the polyphosphinate is poly(1,4-cyclohexanedicarbinyl terephthalate).

A typical amide polymer modified with the present polyphosphinates is nylon 6,6, which is poly(hexamethyleneadipamide). Another amide polymer suitable for this purpose is nylon 6.

A polyurethane resin which can be improved in fire retardant properties by the incorporation therein of the present polyphosphinates is poly-(ethylene N,N'-piperazinedicarboxylate). Other polyurethanes which are suitable are poly(tetramethylenehexamethylenedicarbamate), and another polyurethane is poly[ethylenemethylene bis-(4-phenylcarbamate)].

Dispersion of 8% by weight (relative to the total composition) of the condensed phosphinate of Example 2 in the organic polymers of this example improves the flame retardant properties.

What is claimed is:

1. As compositions of matter, polyphosphinate resins corresponding to the general formula

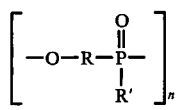

wherein R is a phenylene naphthylene group in which the O substitutent is non-vicinal to the

group, R' is an alkyl group of 1 to 15 carbon atoms or an aryl group of 6 to 15 carbon atoms, and n is from 5 to 50 units.

2. Process for preparing polyphosphinate resins corresponding to the general formula

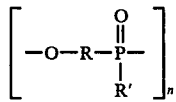

wherein R is a phenylene or naphthylene group in which the O substituent is non-vicinal to the

group, R' is an alkyl group of 1 to 15 carbon atoms or an aryl group of 6 to 15 carbon atoms, and n is from 5 to 50 units, which comprises dehydrohalogenating at a temperature of 50° C to 300° C a monomeric compound having the general formula

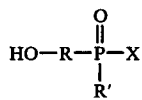

where X is chlorine or bromine.

3. The combination of an organic polymer selected from the group consisting of linear polyesters, and polyamides having recurring amide groups as integral parts of the main polymer chain, together with a polyphosphinate resin corresponding to the general formula

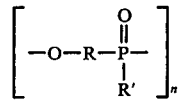

wherein R is a phenylene or naphthylene group in which the O substituent is non-vicinal to the

group, R' is an alkyl group of 1 to 15 carbon atoms or an aryl group of 6 to 15 carbon atoms, and n is from 5 to 50 units.

4. As compositions of matter, polyphosphinate resins corresponding to the general formula

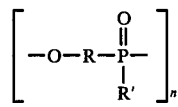

wherein R is a phenylene group in which the O substituent is non-vicinal to the

group, R' is a methyl group and n is from 5 to 50 units.

5. As compositions of matter, polyphosphinate resins corresponding to the general formula

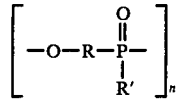

wherein R is a napthylene group in which the O substituent is non-vicinal to

group, R' is an alkyl group of 1 to 15 carbon atoms or an aryl group of 6 to 15 carbon atoms, and n is from 5 to 50 units.

6. The combination of an organic polymer selected from the group consisting of linear polyesters, and polyamides having recurring amide groups as integral parts of the main polymer chain, together with a polyphosphinate resin corresponding to the general formula

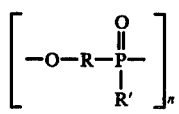

wherein R is a phenylene group in which the O substituent is non-vicinal to the

group, R' is a methyl group, and n is from 5 to 50 units.

7. The combination of an organic polymer selected from the group consisting of linear polyesters, and polyamides having recurring amide groups as integral parts of the main polymer chain, together with a polyphosphinate resin corresponding to the general formula

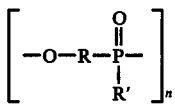

wherein R is a naphthylene group in which the O substituent is non-vicinal to the

group, R' is an alkyl group of 1 to 15 carbon atoms or an aryl group of 6 to 15 carbon atoms, and n is from 5 to 50 units.

8. The combination of polyethylene terephthalate together with a polyphosphinate resin corresponding to the general formula

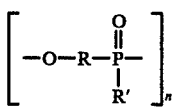

wherein R is a phenylene group in which the O substituent is non-vicinal to the

group, R' is a methyl group, and n is from 5 to 50 units.

9. The combination of polyethylene terephthalate together with a polyphosphinate resin corresponding to the general formula

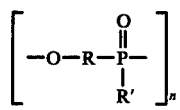

wherein R is a naphthylene group in which the O substituent is non-vicinal to the

group, R' is an alkyl group of 1 to 15 carbon atoms or an aryl group of 6 to 15 carbon atoms, and n is from 5 to 50 units.

10. The combination of a polyamide resin together with a polyphosphinate resin corresponding to the general formula

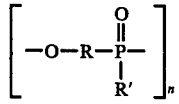

wherein R is a phenylene group in which the O substituent is non-vicinal to the

group, R' is a methyl group, and n is from 5 to 50 units.

11. The combination of polyamide resin together with a polyphosphinate resin corresponding to the general formula

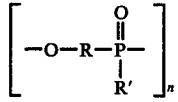

wherein R is a naphthylene group in which the O substituent is non-vicinal to the

group, R' is an alkyl group of 1 to 15 carbon atoms or an aryl group of 6 to 15 carbon atoms, and n is from 5 to 50 units.

* * * * *

UNITED STATES PATENT OFFICE
CERTIFICATE OF CORRECTION

PATENT NO. : 4,087,403
DATED : May 2, 1978
INVENTOR(S) : Kurt Moedritzer

It is certified that error appears in the above-identified patent and that said Letters Patent are hereby corrected as shown below:

Column 2, line 31, "inention" should read --invention--.

Column 7, line 26, Claim 1, the word --or-- should be inserted to read --phenylene or naphthylene--.

Signed and Sealed this

*Twenty-first* Day of *November 1978*

[SEAL]

Attest:

RUTH C. MASON
*Attesting Officer*

DONALD W. BANNER
*Commissioner of Patents and Trademarks*